(12) United States Patent
Trenet et al.

(10) Patent No.: US 9,417,225 B2
(45) Date of Patent: Aug. 16, 2016

(54) TEST SYSTEMS AND PROCESSES FOR EQUIPMENT VIS-A-VIS CONTAMINATED FUEL

(71) Applicant: SNECMA, Paris (FR)

(72) Inventors: Roland Trenet, Champeaux (FR); Jean-Luc Cardot, Saint Quentin (FR); Philippe Chereau, Villeneuve la Guyard (FR); Olivier Defosse, Palaiseau (FR); Jean Yves Perrin, Comb la Ville (FR); Marie-France Rouillard, Guigneville (FR)

(73) Assignee: SNECMA, Paris (FR)

( * ) Notice: Subject to any disclaimer, the term of this patent is extended or adjusted under 35 U.S.C. 154(b) by 373 days.

(21) Appl. No.: 13/962,284

(22) Filed: Aug. 8, 2013

(65) Prior Publication Data

US 2014/0047910 A1 Feb. 20, 2014

(30) Foreign Application Priority Data

Aug. 16, 2012 (FR) ..................... 12 57840

(51) Int. Cl.
| | |
|---|---|
| G01N 1/00 | (2006.01) |
| G01N 33/22 | (2006.01) |
| G01N 1/28 | (2006.01) |
| G01M 15/02 | (2006.01) |
| G01M 15/14 | (2006.01) |
| B01F 5/02 | (2006.01) |
| B01F 5/10 | (2006.01) |

(52) U.S. Cl.
CPC .............. *G01N 33/22* (2013.01); *B01F 5/0268* (2013.01); *B01F 5/10* (2013.01); *G01M 15/02* (2013.01); *G01M 15/14* (2013.01); *G01N 1/28* (2013.01)

(58) Field of Classification Search
CPC ....... G01N 1/10; G01N 1/28; B01L 3/502715
USPC ......................................... 73/64.56
See application file for complete search history.

(56) References Cited

U.S. PATENT DOCUMENTS

| | | | | |
|---|---|---|---|---|
| 3,824,823 | A * | 7/1974 | Pontello | B01D 35/00 73/38 |
| 4,259,022 | A | 3/1981 | Folland | |
| 6,453,257 | B1 * | 9/2002 | Juhasz | B01D 46/44 702/114 |
| 2012/0072194 | A1 | 3/2012 | Arnold et al. | |

FOREIGN PATENT DOCUMENTS

| | | |
|---|---|---|
| DE | 20 2010 014 506 U1 | 1/2011 |
| EP | 2 434 127 A2 | 3/2012 |
| EP | 2 434 127 A3 | 3/2012 |

OTHER PUBLICATIONS

French Preliminary Search Report issued May 14, 2013 in Patent Application No. 1257840 (with English translation of categories of cited documents).

* cited by examiner

*Primary Examiner* — Hezron E Williams
*Assistant Examiner* — Rodney T Frank
(74) *Attorney, Agent, or Firm* — Oblon, McClelland, Maier & Neustadt, L.L.P

(57) ABSTRACT

A test system for equipment using fuel, including a closed supply circuit of the equipment configured to supply contaminated fuel to the equipment is provided. The circuit includes at least one tank including fuel, and a pollution module including on or more vats including fuel contaminated by solid contaminants. The module is configured to introduce contaminated fuel to a section of the supply circuit in which the fuel extracted from the tank circulates towards the equipment. The module also includes an agitating tool configured to take contaminated fuel from the vat and return it to the vat, so as to agitate the contaminated fuel in the vat.

8 Claims, 4 Drawing Sheets

TEST SYSTEMS AND PROCESSES FOR EQUIPMENT VIS-A-VIS CONTAMINATED FUEL

GENERAL TECHNICAL FIELD

The invention relates to a system and a test process for equipment. More particularly, the invention relates to the testing of equipment using fuel to evaluate its resistance and performance with respect to contaminants present in the fuel.

PRIOR ART

In engines, such as aircraft engines, part of the equipment of the engines receives and uses fuel. This can be for example pumps, regulators, or injectors.

When this equipment is being certified, tests have to be conducted during which this equipment receives fuel contaminated by solid contaminants.

For this purpose, test systems are utilised which simulate the environment of the equipment and are configured to supply contaminated fuel to the above equipment.

Figure 1:
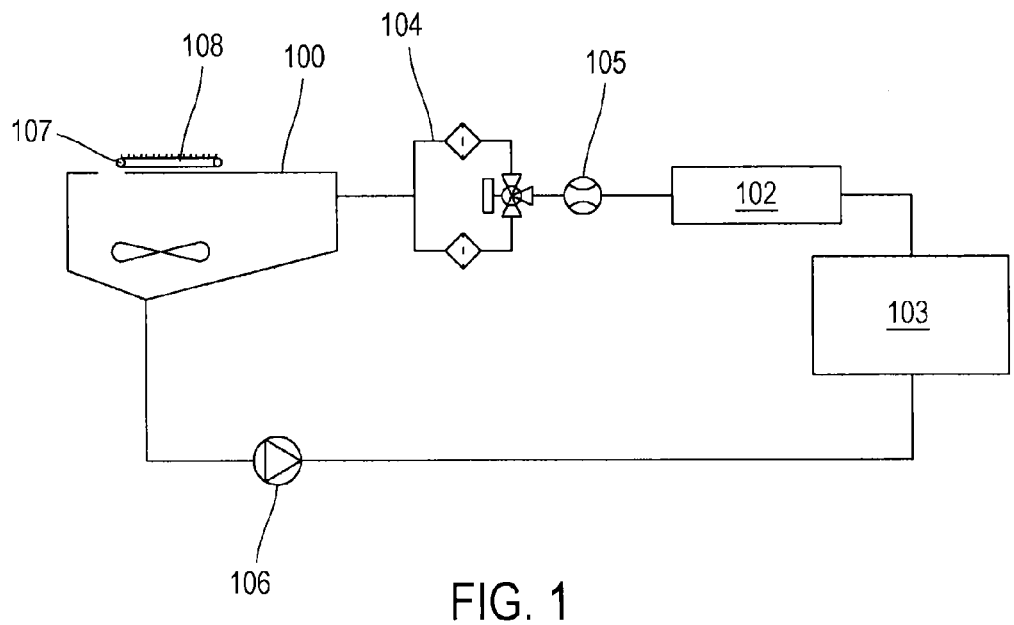

A test system known from the prior art is illustrated in FIG. 1.

The test system comprises a closed supply circuit of the equipment 103 configured to supply contaminated fuel to the equipment 103. The supply circuit comprises a tank 100 filled with fuel, and rolling means 107 via which a plurality of containers 108 can be moved in translation. Each container 108 comprises a predetermined volume of solid contaminants. The contaminants are introduced to the fuel in the tank 100 by placing the containers 108 in translation, which fall into the tank 100. The contaminated fuel is agitated in the tank 100 by way of mechanical means, such as for example a helix.

The contaminated fuel circulates in the supply circuit towards the equipment, especially via a circulation pump 106. The contaminated fuel passes through the equipment. Downstream, the latter meets simulation means 102, simulating the environment downstream of the equipment 103, a flow meter 105, and optionally, a particle filter 104.

The fuel flow feeding the equipment, and the pollution level, must be controlled over time.

This test system has a number of disadvantages.

First, the tank must be open, which contravenes some testing rules which prohibit such due to the risk of explosion.

In addition, given that the number of containers is limited, the test system cannot operate continuously. Once all the containers have been used, the system must be stopped to refill the containers with contaminants.

Also, as the contaminants are introduced via packets, the pollution level of the fuel exhibits major seesawing variations.

Finally, since the contaminants are introduced to the tank, the pollution level of the fuel passing through the equipment cannot be regulated precisely.

PRESENTATION OF THE INVENTION

The invention proposes eliminating the above disadvantages.

For this purpose, the invention proposes a test system for equipment using fuel, characterised in that it comprises a closed supply circuit of the equipment, configured to supply contaminated fuel to the equipment, said circuit comprising:

at least one tank comprising fuel, and
a pollution module, comprising
  one or more vats, comprising fuel contaminated by solid contaminants, said module being configured to introduce contaminated fuel to a section of the supply circuit in which the fuel extracted from the tank circulates towards the equipment, and
  an agitating tool, configured to take contaminated fuel from the vat and return it to the vat so as to hydraulically agitate the contaminated fuel in the vat.

The invention is advantageously completed by the following characteristics, considered alone or in any technically possible combination:

the agitating tool comprises a deflector arranged in the vat;
the vat comprises a conical base;
the pollution module comprises at least one peristaltic pump;
the system comprises a parallel circuit, permanently ensuring a non-zero circulation flow of fuel in the supply circuit;
the supply circuit comprises at least one conduit made of flexible material;
the pollution module comprises a plurality of vats and a control unit for selecting the vat to be operated;
a Pitot tube is arranged in the direction of circulation of the fuel, in a section of the supply circuit located between the vat and a circulation pump of the supply circuit;
the test system comprises a filling connection between the vat and the tank for filling the vat from the fuel contained in the tank.

The invention has numerous advantages.

An advantage of the invention is to propose contaminated fuel in which the contaminants and the liquid fuel are mixed homogeneously.

Another advantage of the invention is to propose a test system which can function continuously.

Yet another advantage of the invention is to propose a test system in which the pollution level is regulated, even when the fuel flow is variable. In particular, the pollution level can be adapted and adjusted precisely.

Finally, another advantage of the invention is to reduce contaminant deposits in the supply circuit.

PRESENTATION OF THE FIGURES

Figure 2:
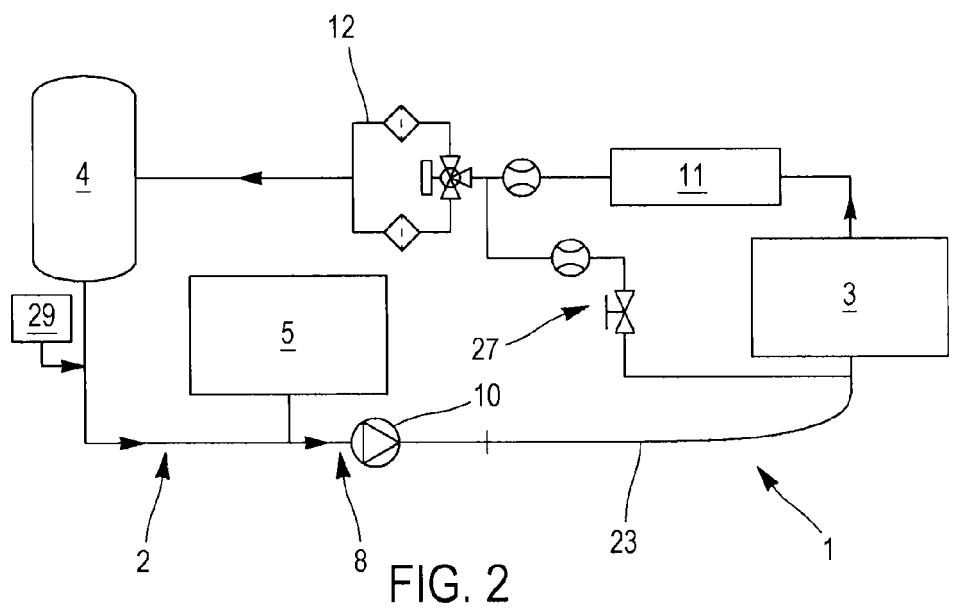
Figure 3:
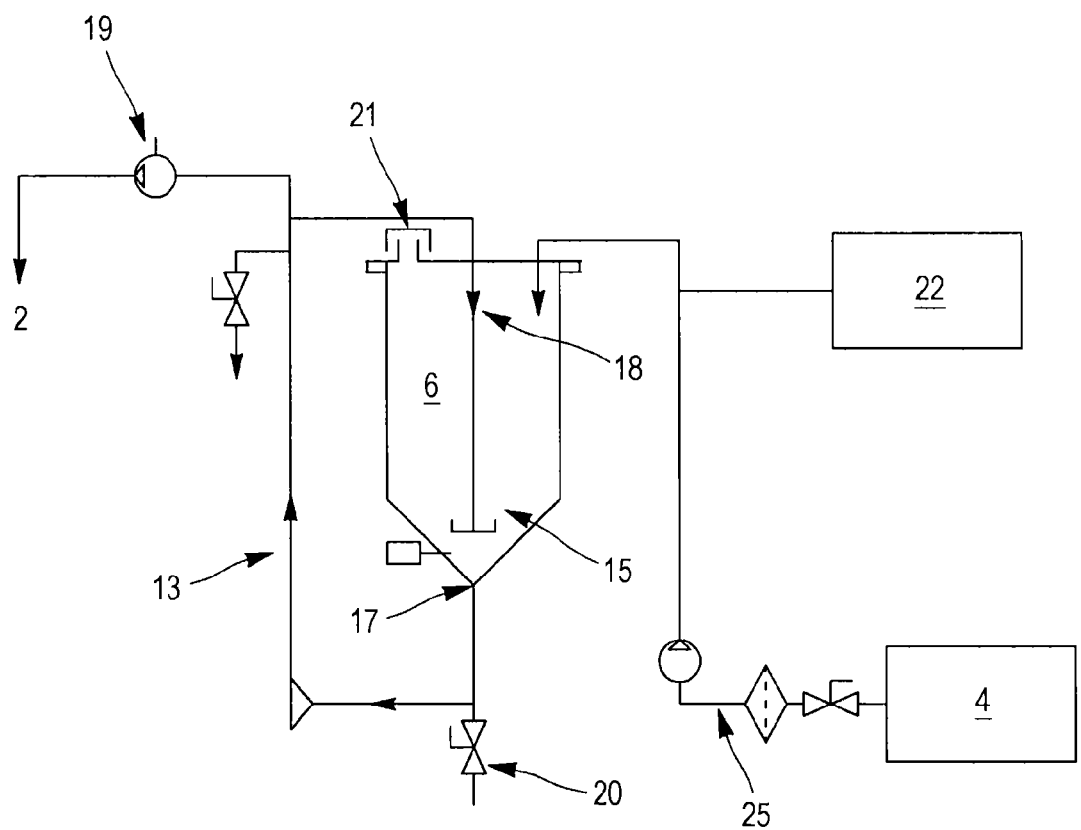
Figure 4:
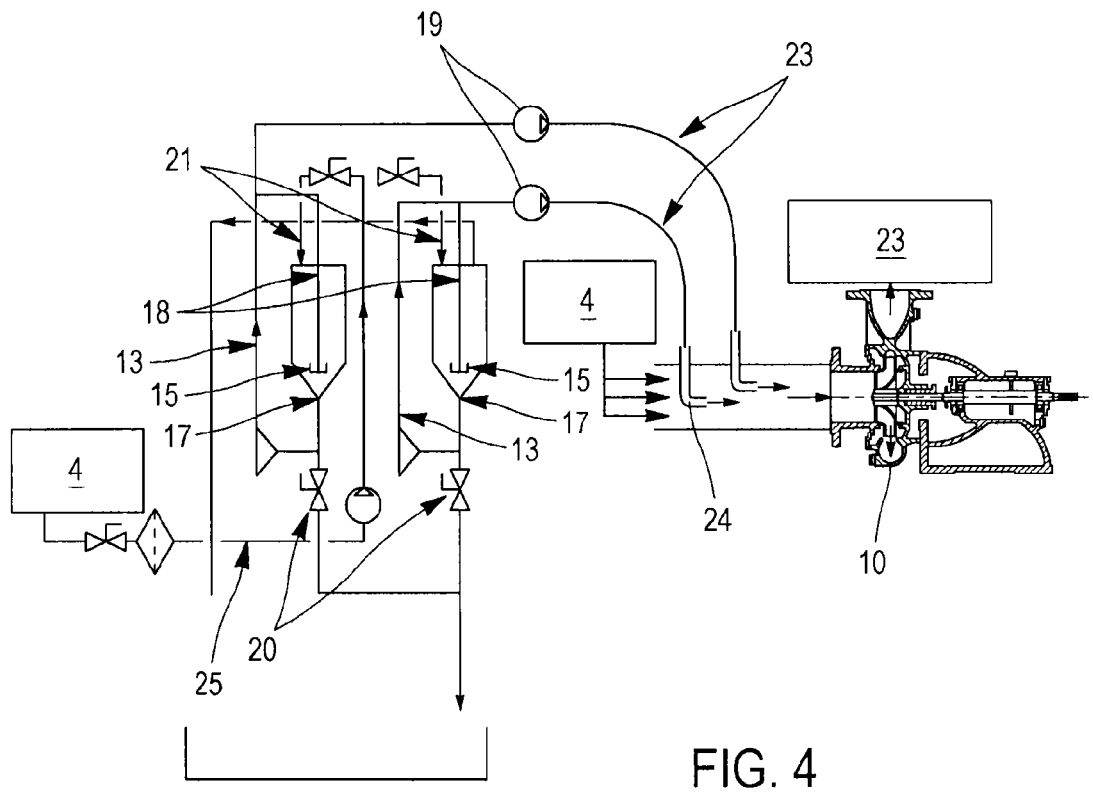
Figure 5:
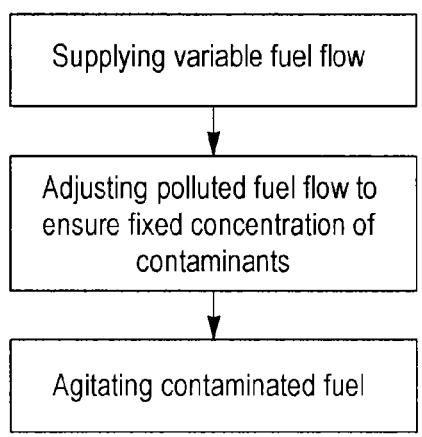
Figure 6:
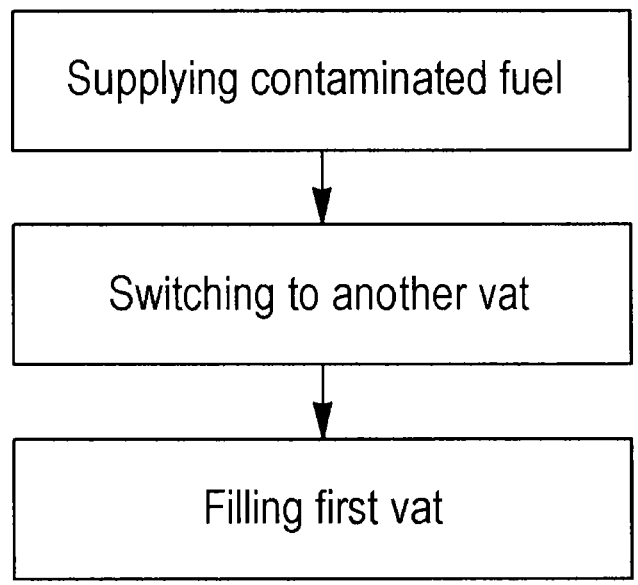

Other characteristics, aims and advantages of the invention will emerge from the following description which is purely illustrative and non-limiting and which must be considered with respect to the attached diagrams, in which:

FIG. 1, already mentioned, is a schematic representation of a test system according to the prior art;
FIG. 2 is a representation of an embodiment of a test system according to the invention;
FIG. 3 is a representation of another embodiment of a pollution module according to the invention;
FIG. 4 is a representation of another embodiment of a pollution module according to the invention;
FIG. 5 is a representation of steps of an embodiment of a test process;
FIG. 6 is a representation of steps of another embodiment of a test process.

DETAILED DESCRIPTION

The Test System

FIG. 2 illustrates an embodiment of a test system 1 of equipment 3. This equipment utilises fuel, and the test system tests the reaction of the equipment to use of contaminated fuel. This equipment can be for example pumps, regulators, injectors, valves, jacks, flow meters, or other engine parts. "Equipment using fuel" means equipment which, in operation, receives fuel, or which fuel passes through, or uses fuel during operation, or consumes fuel.

The system 1 comprises a closed supply circuit 2 of the equipment 3, configured to supply contaminated fuel to the equipment 3. If needed, the system 1 also comprises the equipment itself.

The circuit 2 comprises at least one tank 4 comprising fuel.

In the case where the aim is to test equipment 3 of an aircraft engine, the fuel is kerosene.

The circuit 2 also comprises a pollution module 5, embodiments of which are illustrated in FIGS. 3 and 4.

In conventional terms, the circuit 2 can also comprise a circulation pump 10, ensuring pressurisation and circulation of fuel in the supply circuit, simulation means 11, simulating the environment downstream of the equipment 3, and a particle filter 12.

The pollution module 5 comprises one or more vats 6, comprising fuel contaminated by contaminants, comprising at least solid contaminants.

This contaminated fuel therefore comprises liquid fuel, of the same type (or optionally different) as that in the tank 4, and solid contaminants.

These solid contaminants are for example sand, particles of metal, silica and/or iron oxide, in different granulometries. The nature of the solid contaminants depends on tests to be conducted and equipment to be tested.

The concentration of solid contaminants in the vat 6 is greater than the concentration of solid contaminants to be supplied at the input of the equipment by means of the supply circuit 2. By way of non-limiting example, if the aim is to supply contaminated fuel with a concentration of between 1 and 10 mg/L to the equipment 3, contaminated fuel in the vat 6 with a concentration of between 0.5 and 1 g/L could be used.

The pollution module 5 is configured to introduce contaminated fuel to a section 8 of the supply circuit in which the fuel extracted from the tank 4 circulates towards the equipment 3.

In this way, the pollution module 5 does not introduce the contaminated fuel directly to the tank 4, but to a section 8 of the supply circuit 2 located downstream from the tank 4, relative to the direction of circulation of the fuel.

It is preferable for the pollution module 5 to introduce contaminated fuel to a section of the supply circuit 2 near the equipment 3 to minimise solid contaminant losses in the conduits of the supply circuit 2.

In the embodiment of FIG. 2, the pollution module 5 introduces the contaminated fuel upstream of the circulation pump 10, as the pressure in the circuit 2 is lower there than downstream from said pump, which makes inserting the contaminated fuel easier. However, this is merely a non-limiting embodiment.

The pollution module 5 also comprises an agitating tool 13, configured to take contaminated fuel from the vat 6 and return it to the vat 6 so as to hydraulically agitate the contaminated fuel in the vat. Taking fuel from the bottom of the vat 6 and returning it to the vat 6 ensure hydraulic agitation in the vat by mixing.

The agitating tool 13 agitates the contaminated fuel so as to keep the solid contaminants suspended. In fact, if the solid contaminants are deposited at the bottom of the vat 6 the concentration of solid contaminants is no longer homogeneous in the fuel of the vat 6. This lack of homogeneity impairs control of the concentration of solid contaminants to be sent to the equipment 3, and reduces the performance of the test process.

The agitating tool 13 therefore gives better control of the concentration in contaminants in the vat 6, and in the supply circuit 2.

In an embodiment, the agitating tool 13 comprises a deflector 15 arranged in the vat 6. In this case, the agitating tool 13 is configured to take contaminated fuel from the vat 6 and return it in the direction of the deflector 15 so as to cause ascending agitation motion of the contaminated fuel. This is closed-circuit hydraulic agitation.

The deflector 15 has a mechanical form for causing an ascending motion to the contaminated fuel when the latter is returned to the vat 6 by the agitating tool 13. The deflector 15 generally has a cavity oriented to the top of the vat 6, such as a cup for example.

Agitation and suspending of the solid contaminants are even further improved.

Hydraulic agitation also prevents the unacceptable presence of deposits of solid contaminants, as is the case at the bottom of mechanical mixers.

By way of example, a vat 6 containing around 200 liters can be used. In this case, the hydraulic agitation ensured by the agitating tool 13 is typically around 8,000 L/h.

In an embodiment, the vat 6 comprises a base which is not flat, and in particular, a conical base. This limits deposits of solid contaminants at the base of the vat. Therefore, the homogeneity of the concentration of solid contaminants is higher in the vat 6.

In an embodiment, the agitating tool 13 comprises a sampling input arranged at the base 17 of the vat 6, and a return output for fuel in the vat arranged in a zone 18 of the vat 6.

Because of the agitating tool, the homogeneity of the contaminated fuel and the agitation are improved.

In an embodiment, the pollution module 5 comprises at least one peristaltic pump 19, or a plurality of these pumps.

A peristaltic pump is a pump in which the liquid is contained in flexible a tube, entrained by a system pressing the tube inside the pump. Using this pump avoids contact between the contaminated fuel and the mechanical systems, reducing risks of unwanted deposits of solid contaminants, and reduces the risk of wear on the mechanical elements of the pump.

The peristaltic pump 19 is configured to take contaminated fuel from the vat 6 to the supply circuit 2. In an embodiment, the pump 19 is connected, on the one hand to a conduit of the agitating tool 13 in which the contaminated fuel recirculates for agitation, and on the other hand to the supply circuit 2. The conduit connecting the conduit of the agitating tool 13 to the pump 19 is introduced to this conduit at such a depth to avoid the edges of the conduit, in which the fuel can tend to stagnate.

Once this sampling is complete, the peristaltic pump 19 sends the contaminated fuel to the section 8 of the supply circuit 2 in which the fuel extracted from the vat 4 circulates towards the equipment 3.

The pollution module 5 also comprises an emptying valve 20 for emptying the vat 6 by gravity, and an opening 21 for introducing solid contaminants to the vat 6.

Advantageously, the test system 1 comprises a filling connection 25 between the vat 6 and the tank 4 for filling the vat 6 from the fuel contained in the tank 4. In fact, the fuel injected by the pollution module 5 into the supply circuit 2 terminates each cycle in the tank 4, after having passed through the equipment 3, which retains some of the contaminants, the simulation means 11 which also retain some, and finally the particle filter 12. The tank 4 therefore risks overflowing during prolonged use of the test system 1 in closed circuit, requiring the system to be stopped by an operator.

In an ingenious way the filling connection 25 ensures continuity of operation of the system 1 by filling the vat 6 from the tank 4, avoiding the risk of saturation of the tank 4.

In an embodiment, the test system 1 also comprises at least one Pitot tube 24, arranged in the direction of circulation of the fuel, in a section of the supply circuit 2 located between the vat 6 and the circulation pump 10 of the supply circuit. This Pitot tube 24 improves the mixing and dilution between the fuel originating from the tank 4 and the contaminated fuel supplied by the pollution module 5. In particular, the mixing and dilution are improved in the suction pipe of the circulation pump 10.

In an embodiment, the supply circuit 2 comprises one or more conduits 23 made of flexible material, arranged in a section of the supply circuit 2 located between the tank 4 and the equipment 3, or between the vat 6 and the pump 10, or between the pump 10 and the equipment 3. An example of flexible material is Tygon™. This produces a curved conduit. Advantageously, the conduit is monobloc and the diameter is reduced relative to the conduits used in the prior art, which increases the speed of the fuel and reduces deposits, especially between the circulation pump and the equipment.

These conduits limit the highly angular sections, the sharp elbow bends and the roughness at the connections due to higher radii of curvature, avoiding blockage of particles.

Consequently, unwanted deposits of solid contaminants are reduced.

These conduits are generally arranged between the circulation pump 10 and the equipment 3.

Similarly, in an embodiment the conduits of the supply circuit 2 are arranged going down to reduce deposits.

In an embodiment, the test system 1 also comprises a parallel circuit 27, ensuring a non-zero circulation flow of fuel in the supply circuit 2, said parallel circuit being connected on the one hand to the supply circuit 2 upstream of the equipment 3, and on the other hand to the supply circuit downstream of the equipment 3, relative to the direction of circulation of the fuel.

When the test system 1 is controlled such that the outlet flow of the tank 4 to the equipment 3 is zero, or virtually zero, it has been noted that the fuel stagnating between the circulation pump 10 and the equipment 3 was causing deposit of solid contaminants in the conduits of the circuit. The parallel circuit 27 ensures non-zero circulation flow of the fuel in the circuit, even when the flow passing through the equipment 3 is zero. The circuit 27 comprises especially valves and one or more flow meters.

In an embodiment, the pollution module 5 comprises a plurality of vats 6. The module 5 also comprises a control unit 22, configured to control the pollution module 5 so as to introduce contaminated fuel to a section 8 of the supply circuit in which the fuel extracted from the tank circulates towards the equipment, from one or more of these vats. This control unit 22 operates the vats 6 separately, alternatively, or simultaneously. The same applies for hydraulic agitation. As explained hereinbelow, this ensures continuous operation of the test system 1. This control unit can form part of a central control unit 29 of the test system 1, or be separate.

In general, the test system 1 comprises one or more control units 29 for managing the different elements of the system, according to what has been described earlier: flow, opening of valves, operation of pumps, managing sensors, etc. These control units comprise one or more processors, one or more memories storing control programs and where required a monitor and means of interacting with an operator. The control parameters of the control units can be for example predefined prior to each test campaign.

Test Procedures $1^{st}$ Example

In this example, the fuel is injected into the supply circuit 2 from the tank 4. The pollution module 5 is controlled and supplies contaminated fuel from one or more of its vats 6 to a section of the supply circuit 2 located downstream from the tank.

The contaminated fuel is agitated permanently in the vats 6 of the module 5, by way of the agitating tool 13.

The contaminated fuel circulates in the supply circuit 2 and is sent to the equipment 3.

After passing through the equipment 3 and where required the simulation means 11, the fuel is filtered and returns to the tank 4. The cycle is repeated as necessary.

Observation measurements (temperature, pressure, etc.) on the equipment 3 verify resistance of the equipment 3 to the contaminated fuel.

$2^{nd}$ Example

In this example, the test system comprises a pollution module 5 comprising several vats 6.

Each vat 6 has for example a volume of around 200 liters.

These vats 6 contain fuel which is polluted by 100 g of contaminants, or a concentration of 0.5 g/L. This fuel, now highly polluted, is sent from the vats 6 to the supply circuit 2 by means of two peristaltic pumps equipped with conduits made of Tygon™. The flow can be regulated by variation of the pump rate, between 0.7 and 7.5 L/h.

The vats 6 are fitted with level sensors which detect when the contents of the vat reach a minimal volume of 5 L.

Since the sensor detects that the volume in the vat in use has reached the minimal volume, the control unit executes automatic switching to start up the other vat. The system operates continuously, given that an operator can initiate filling of one vat while the other is running, and vice versa. This filling is ensured via the connection 25 linking the vat 6 to the tank 4.

The contaminants are kept in suspension by hydraulic agitation of 8,000 L/h.

Testing the equipment can consist of measuring the concentration of contaminants upstream and downstream of the equipment, or in the equipment itself. Observations on the resistance of the equipment can also be made (temperature, pressure, etc.).

$3^{rd}$ Example

In another embodiment, the test system 1 comprises one or more vats 6.

A test process (cf. FIG. 5) comprises the step consisting of controlling the fuel flow passing through the equipment 3 to supply variable fuel flow to the equipment 3 over time.

A control unit 29 of the test system 1 manages this variable flow, by control of the equipment 3, especially via one or more regulators placed in the equipment or upstream of the equipment 3.

The process also comprises the steps consisting of:
introducing contaminated fuel from the vat 6 to the section of the supply circuit in which the fuel extracted from the tank 4 circulates towards the equipment, and
controlling the flow of contaminated fuel passing through the equipment 3 to obtain contaminated fuel passing through the equipment 3 with a fixed concentration of contaminants over time.

The control unit 29 therefore manages the flow of contaminated fuel passing through the equipment to obtain variable flow of contaminated fuel passing through the equipment, and maintain a fixed concentration of contaminants.

During the test process, the agitating tool takes contaminated fuel from the vat and returns it to the vat so as to agitate the contaminated fuel in the vat and maintain uniform concentration of contaminants.

This fine management of the contaminant concentration is possible despite the variable fuel flow thanks to the test system according to the invention in which the homogeneity of the contaminated fuel is improved, and into which the contaminants are introduced, no longer in the tank, but in a section located downstream from the tank. The fact of stopping the test process engenders contaminant deposits in the supply circuit, but this is avoided here.

In an embodiment (cf. FIG. 6), which can be combined or not with the preceding embodiment, the control unit 29 manages the pollution module 5 so as to introduce contaminated fuel from at least one first vat, then from at least one second vat when the first vat contains a volume of contaminated fuel less than a threshold to ensure a continuous test process.

Continuous operation is ensured without the need to stop the test process for filling or cleaning purposes.

Whereas the second vat is used in place of the first vat, the first vat is refilled via the tank 4, and so on.

The test system therefore produces contaminated fuel in which the contaminants and the liquid fuel are mixed uniformly.

In addition, the test system can operate continuously, and the pollution level is under control, even when the fuel flow is variable in the supply circuit.

In particular, because of the test system according to the invention the pollution level can be adapted and adjusted precisely.

Finally, the contaminant deposits in the supply circuit are reduced, which improves performance and reduces costs of test campaigns.

The invention claimed is:

1. A test system for equipment using fuel, comprising:
   a closed supply circuit of the equipment, configured to supply contaminated fuel to the equipment, said circuit comprising:
      at least one tank comprising fuel, and
      a pollution module, comprising
         a vat comprising fuel contaminated by solid contaminants, the vat comprising top and a bottom,
         said module being configured to introduce contaminated fuel to a section of the supply circuit in which the fuel extracted from the tank circulates towards the equipment, and
         an agitating tool configured to take contaminated fuel from the vat and return the contaminated fuel to the vat to hydraulically agitate the contaminated fuel, in the vat,
         the agitating tool comprising a deflector arranged in the vat, said deflector having a cavity oriented to the top of the vat,
         the agitating tool being configured to take contaminated fuel from the vat and to return the contaminated fuel in the direction of the deflector so as to cause ascending agitation motion of the contaminated fuel.

2. The test system according to claim 1, wherein the vat comprises a conical base.

3. The test system according to claim 1, wherein the pollution module comprises at least one peristaltic pump configured to:
   take contaminated fuel from the vat, and
   send the contaminated fuel to a section of the supply circuit in which the fuel extracted from the vat circulates towards the equipment.

4. The test system according to claim 1, further comprising a parallel circuit configured to ensure non-zero circulation flow of fuel in the supply circuit, said parallel circuit being connected to the supply circuit upstream of the equipment and to the supply circuit downstream of the equipment.

5. The test system according to claim 1, wherein the supply circuit comprises at least one conduit made of flexible material.

6. The test according to claim 1, wherein the pollution module comprises:
   a plurality of vats, and
   a control unit, configured to control the pollution module so as to introduce contaminated fuel to a section of the supply circuit in which the fuel extracted from the tank circulates towards the equipment from one or more of the vats.

7. The test system according to claim 1, further comprising a Pitot tube, arranged in the direction of circulation of the fuel, in a section of the supply circuit located between the vat and a circulation pump of the supply circuit.

8. The test system according to claim 1, further comprising a filling connection between the vat and the tank for filling of the vat with fuel contained in the tank.

* * * * *